United States Patent [19]
Place et al.

[11] Patent Number: 5,919,474
[45] Date of Patent: Jul. 6, 1999

[54] TRANSURETHRAL ADMINISTRATION OF VASOACTIVE AGENTS TO TREAT PERIPHERAL VASCULAR DISEASE, RELATED VASCULAR DISEASES, AND VASCULAR IMPOTENCE ASSOCIATED THEREWITH

[75] Inventors: Virgil A. Place, Kawaihae, Hi.; Mark S. Hanamoto, Belmont, Calif.; Paul C. Doherty, Jr., Cupertino, Calif.; Alfred P. Spivack, Menlo Park, Calif.; Neil Gesundheit, Los Altos, Calif.; Sean R. Bennett, Denver, Colo.

[73] Assignee: VIVUS, Inc., Mountain View, Calif.

[21] Appl. No.: 08/959,063

[22] Filed: Oct. 28, 1997

[51] Int. Cl.$^6$ .............................. A61F 6/06; A61F 13/02
[52] U.S. Cl. ............................................ 424/430; 424/434
[58] Field of Search ...................................... 424/430, 434

[56] References Cited

U.S. PATENT DOCUMENTS

| | | |
|---|---|---|
| 4,454,138 | 6/1984 | Goring . |
| 4,478,822 | 10/1984 | Haslam et al. . |
| 4,610,868 | 9/1986 | Fountain et al. . |
| 4,638,011 | 1/1987 | Das . |
| 4,772,603 | 9/1988 | Evans et al. . |
| 4,784,999 | 11/1988 | Angersbach et al. . |
| 4,801,587 | 1/1989 | Voss et al. . |
| 4,968,719 | 11/1990 | Brevetti . |
| 5,242,391 | 9/1993 | Place et al. . |
| 5,272,147 | 12/1993 | Bell et al. . |
| 5,321,029 | 6/1994 | Maschler et al. . |

FOREIGN PATENT DOCUMENTS

WO 90/02545 3/1990 WIPO .
WO 91/16021 10/1991 WIPO .

OTHER PUBLICATIONS

Basile et al. (1994), "Medical Treatment of Neurogenic Impotence," *Sexual Disabilities* 12(1):81–94.
Coffmann et al. (1972), "Failure of Vasodilator Drugs in Arteriosclerosis Obliterans," *Ann. Intern. Med.* 76:35.
Hansteen et al. (1974), "Vasodilator Drugs in the Treatment of Peripheral Arterial Insufficiency," *Acta Med. Scand.* [*Suppl.*] 556:3.
Mashiah et al. (1978), "Drug Therapy in Intermittent Claudication: an Objective Assessment of the Effects of Three Drugs on Patients with Intermittent Claudication," *Br. J. Surg.* 65:342.
Porter et al. (1982), "Pentoxifylline Efficacy in the Treatment of Intermittent Claudication: Multicenter Controlled Double–blind Trial with Objective Assessment of Chronic Occlusive Arterial Disease Patients," *Am. Heart J.* 104:66.

*Primary Examiner*—Carlos Azpuru
*Attorney, Agent, or Firm*—Dianne E. Reed; Reed & Associates

[57] ABSTRACT

A method for treating peripheral vascular disease (PVD), related vascular diseases, and vascular impotence associated with such diseases, is provided. The method involves transurethral administration of a pharmaceutical formulation containing a selected vasoactive agent within the context of an effective dosing regimen. Preferred vasoactive agents are vasodilating agents selected from the group consisting of naturally occurring prostaglandins, synthetic prostaglandin derivatives, and combinations thereof. The pharmaceutical formulations used in conjunction with the novel method may also contain enzyme inhibitors, transurethral permeation enhancers, carriers, preservatives, surfactants, and the like. Kits and pharmaceutical formulations are provided as well.

42 Claims, 1 Drawing Sheet

TRANSURETHRAL ADMINISTRATION OF VASOACTIVE AGENTS TO TREAT PERIPHERAL VASCULAR DISEASE, RELATED VASCULAR DISEASES, AND VASCULAR IMPOTENCE ASSOCIATED THEREWITH

TECHNICAL FIELD

This invention relates generally to the administration of vasoactive agents in the treatment of vascular disease. More particularly, the invention relates to methods and drug delivery systems for transurethral administration of a vasoactive agent, preferably a vasodilating agent such as a prostaglandin, in the treatment of peripheral vascular disease ("PVD") and related vascular diseases.

BACKGROUND

Vascular disease of the limbs caused by organic arterial obstruction (e.g., arteriosclerosis obliterans) generally involves segmental arteriosclerotic narrowing, and the concomitant obstruction of the lumen in arteries supplying the extremities, particularly in peripheral body parts such as the limbs. In the progression of the disease, organic obstruction leads to occlusion of the artery, which in turn leads to an interruption of the vascular supply to a tissue or organ, resulting in ischemia or necrosis. Ross, R. (1986) *N. Engl. J. Med.* 314:488. PVD becomes clinically manifest usually between the ages of 50 and 70, and is more prevalent in men than in women. The lower limbs are more frequently involved than the upper limbs, and the most commonly affected vessel is the superficial femoral artery. Schadt et al. (1961) *JAMA* 175:937

Clinical manifestations of PVD include intermittent claudication, pain at rest, and trophic changes in the involved tissue or limb. Coffman, J. D. (1979) *Prog. Cardiovasc. Dis.* 22:53. A related clinical condition, Leriche's syndrome, involves isolated aortoiliac disease, and generally manifests as intermittent claudication of the lower back, buttocks, and thigh or calf muscles.

In addition, atherosclerotic PVD, involving the distal aortoiliac arteries and trauma to those vessels, are thus a common cause of vascular impotence. Individuals suffering from such vascular impotence generally have diminished or substantially absent femoral pulses, and generally present with Leriche's syndrome, although claudication may be absent in some cases. Furthermore, atherosclerotic macro- and microvascular disease are major factors contributing to erectile dysfunction in from 30 to 50 per cent of diabetic men who develop impotence.

PVD has been treated medically with some success, using agents such as pentoxifylline, which acts by increasing red cell membrane deformability, thereby reducing blood viscosity (Porter et al. (1982) *Am. Heart J.* 104:66), although other investigators have not found such viscosity-reducing agents to be efficacious (Mashiah et al. (1978) *Br. J. Surg.* 65:342). Other approaches in the treatment of PVD have employed oral, parenteral or intravenous administration of vasodilators (Hansteen et al. (1974) *Acta Med. Scand.* [*Suppl.*] 556:3, Coffmann et al. (1972) *Ann. Intern. Med.* 76:35), L-carnitine (U.S. Pat. No. 4,968,719 to Brevetti), diuretics such as 1,3-di-n-butyl-7-(2-oxypropyl)xanthine (U.S. Pat. No. 4,784,999 to Angersbach et al.), xanthines and xanthine derivatives (U.S. Pat. Nos. 5,321,029 to Maschler et al. and 4,454,138 to Goring), selective inhibitors of cyclic guanosine 3',5'-monophosphate phosphodiesterase ("cGMP PDE") (U.S. Pat. No. 5,272,147 to Bell et al.), and various classes of chromanols, chromenes and chromans having anti-hypertensive activity (U.S. Pat. No. 4,772,603 to Evans). However, each approach has achieved limited success. Accordingly, there remains a need in the art to provide a more effective method of treating PVD, and particularly PVD-associated vascular impotence.

The present invention is directed to a novel method of treating the aforementioned vascular diseases as well as a novel method for treating vascular impotence as may be associated with such diseases. The treatment involves transurethral administration of a vasoactive agent, particularly a vasodilating agent, as will be described in detail herein.

Transurethral administration of pharmacologically active agents has been described. For example, U.S. Pat. No. 4,478,822 to Haslam et al. relates to a controlled release, thermosetting gel formulation for delivering drugs into a body cavity such as the urethra. Also, U.S. Pat. No. 4,610,868 to Fountain et al. describes a biodegradable lipid matrix composition for administering a drug, wherein the composition is stated to be deliverable through the urethra. Basile et al. (1994), "Medical Treatment of Neurogenic Impotence," *Sexual Disabilities* 12(1):81–94 describes the intraurethral administration of drugs. PCT Publication No. WO91/16021, U.S. Pat. No. 4,801,587 to Voss et al., and U.S. Pat. No. 5,242,391 to Place et al. relate to the treatment of erectile dysfunction by administration of vasoactive agents into the male urethra. While these references mention urethral drug delivery, the potential importance of administering specific drugs in this manner to induce a desired local or systemic effect has only recently been recognized. Further, applicant is unaware of any art disclosing the effectiveness of transurethral administration of vasoactive agents in the treatment of PVD or PVD-associated vascular impotence.

Accordingly, the present invention provides for an effective method of treating peripheral vascular disease and PVD-associated vascular impotence, by transurethrally administering a vasoactive agent to an individual in need of such treatment. The invention avoids the limitations encountered with other modes of administration, and furthermore, enables the use of lower drug doses than would typically be required with alternative administration techniques.

SUMMARY OF THE INVENTION

Accordingly, it is a primary object of the invention to provide a novel method for treating PVD or a related vascular disease by transurethrally administering a therapeutically effective amount of a selected vasoactive agent to an individual suffering from such a disease.

It is another object of the invention to provide a method for treating vascular impotence associated with PVD or a related vascular disease by transurethrally administering a therapeutically effective amount of a vasoactive agent to an individual in need of such treatment.

It is still another object of the invention to provide a method for treating PVD or a related vascular disease by transurethrally administering to an individual suffering from such a disease, within the context of a predetermined dosing regimen, a vasodilating agent selected from the group consisting of naturally occurring prostaglandins, synthetic prostaglandin derivatives, and mixtures thereof.

It is yet another object of the invention to provide a method for treating vascular impotence associated with PVD or a related vascular disease by transurethrally administering to an afflicted individual a vasodilating agent selected from the group of naturally occurring prostaglandins, synthetic prostaglandin derivatives, and suitable mixtures thereof.

It is a further object of the invention to provide such a method in which the vasodilating agent is administered in conjunction with one or more compounds effective to inhibit enzymes which could degrade or metabilize the active agent.

It is still a further object of the invention to provide such methods in which the vasoactive agent is administered in conjunction with a transurethral permeation enhancer.

It is yet a further object of the invention to provide pharmaceutical formulations for carrying out the aforementioned methods of treatment.

It is yet a further object of the invention to provide a kit capable of use by an individual in carrying out the present method of treatment.

Additional objects, advantages and novel features of the invention will be set forth in part in the description which follows, and in part will become apparent to those skilled in the art upon examination of the following, or may be learned by practice of the invention.

In a first aspect of the invention, a pharmaceutical formulation containing a vasoactive agent, generally a vasodilator, is administered to the urethra of an individual suffering from PVD or a related vascular disease. Administration of the pharmaceutical formulation is carried out within the context of a predetermined dosing regimen such that the agent is effective in the treatment of PVD or a related vascular disease such as Leriche's syndrome. This aspect of the invention extends to the treatment of vascular impotence associated with PVD or related vascular diseases.

In another aspect of the invention, a kit is provided to assist an individual in drug administration. Generally, the kit will include the following components: the pharmaceutical formulation comprising the vasoactive agent to be administered; a device for effecting transurethral delivery of the pharmaceutial formulation; a container housing the vasoactive agent during storage and prior to use; and written instructions for carrying out transurethral drug administration in a manner effective to treat PVD, a related vascular disease, or vascular impotence as may be associated therewith.

In a further aspect of the invention, a pharmaceutical formulation is provided for carrying out the present methods for treating PVD, related vascular diseases, or vascular impotence associated with such diseases. The pharmaceutical composition is a urethral dosage formulation comprising an effective amount of a vasoactive agent, preferably a vasodilating agent, optionally one or more compounds effective to inhibit enzymatic degradation of the vasoactive agent in situ and/or a transurethral administration enhancer, and carriers or excipients suited to transurethral drug administration. Other types of components may be incorporated into the formulation as well, e.g., excipients, surfactants, preservatives (e.g., antioxidants), stabilizers, enzyme inhibitors, chelating agents, and the like, as will be appreciated by those skilled in the art of pharmaceutical formulation preparation and drug delivery.

DETAILED DESCRIPTION OF THE INVENTION

Figure 1:
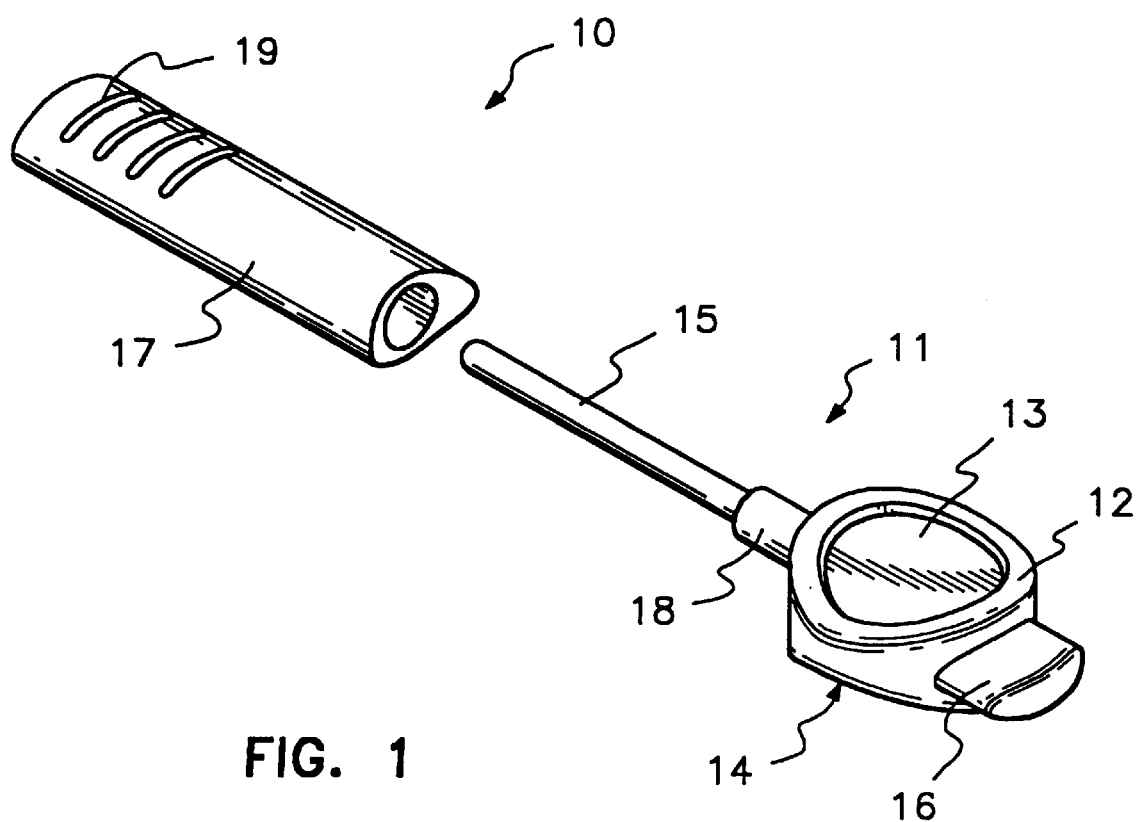
FIG. 1 is an exploded view of one embodiment of a transurethral therapeutic device which may be used in conjunction with the present method.

Before describing the present invention in detail, it is to be understood that this invention is not limited to delivery of specific vasoactive agents, pharmaceutical carriers, drug delivery systems, or the like, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "a vasodilating agent" includes a mixture of two or more such drugs, reference to "an enzyme inhibitor" includes mixtures of two or more enzyme inhibitors, reference to a "transurethral permeation enhancer" includes mixtures of two or more enhancers, and the like.

In describing and claiming the present invention, the following terminology will be used in accordance with the definitions set out below.

The terms "active agent," "drug" and "pharmacologically active agent" are used interchangeably herein to refer to a chemical material or compound which, when administered to an organism (human or animal) induces a desired pharmacologic effect. In the method of the present invention, the terms refer to a compound which is capable of being delivered transurethrally. Included are derivatives and analogs of those compounds or classes of compounds specifically mentioned which also induce the desired pharmacologic effect.

The terms "transurethral," "intraurethral" and "urethral" to specify the preferred mode of administration herein are used interchangeably to refer to delivery of the drug into the urethra such that drug contacts and passes through the wall of the urethra. As noted elsewhere herein, the present method preferably involves delivery of the drug at least about 3 cm and more preferably at least about 7 cm into the urethra.

"Penetration enhancement" or "permeation enhancement" as used herein relates to an increase in the permeability of the skin or mucosal tissue to a selected pharmacologically active agent, i.e., so that the rate at which the drug permeates through the skin or mucosal tissue is increased. "Transurethral permeation enhancers" increase the permeability of the urethral wall to drugs administered as described herein.

The terms "carriers" or "vehicles" and "excipients" as used herein refer to inert materials which may be included in the pharmaceutical formulations administered herein, including any such materials known in the art, e.g., any liquid, gel, solvent, liquid diluent, solubilizer, or the like, which is nontoxic, does not interact with other components of the pharmaceutical formulations in a deleterious manner, and which is suitable for administration into the urethra.

By an "effective" amount of a drug or pharmacologically active agent is meant a nontoxic but sufficient amount of the drug or agent to provide the desired effect.

By "PVD-associated" vascular impotence or vascular impotence "associated" with PVD or other vascular diseases is meant vascular impotence resulting from or occurring concomitantly with the disease.

The term "synthetic prostaglandin derivatives" is intended to encompass known or unknown compounds related to the naturally occurring prostaglandins, $PGE_0$, $PGE_1$, $PGA_1$, $PGB_1$, $PGF_{1a}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3a}$, $PGI_2$, and which are chemically synthesized using starting materials other than one of the naturally occurring prostaglandins. The term "semisynthetic prostaglandin derivatives" refers to known or unknown compounds related to the aforementioned naturally occurring prostaglandins which are synthesized therefrom. The synthetic and semisynthetic prostaglandin derivatives useful in conjunction with the present invention will typically although not necessarily have the structure of Formula (I)

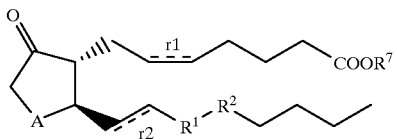

wherein:

$R^1$ and $R^2$ may be the same or different and are selected from the group consisting of

in which $R^3$ and $R^4$ are independently selected from the group consisting of hydrogen, lower alkyl and $OR^5$ in which $R^5$ is selected from the group consisting of hydrogen, tetrahydropyranyl, tetrahydrofuranyl, triloweralkylsilyl, 1-methyl-1-methoxyethyl, 1-methyl-1-ethoxyethyl and —(CO)—$R^6$, wherein $R^6$ is hydrogen, lower alkyl, or halogen-substituted lower alkyl;

A is selected from the group consisting of

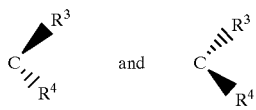

wherein $R^5$ is as defined above;

$r^1$ and $r^2$ represent optional double bonds; and $R^7$ is $R^5$, lower alkyl or lower alkenyl.

Active Agents for Treating PVD, Related Vascular Diseases, and Vascular Impotence Associated Therewith In order to carry out the method of the invention, a vasoactive agent, preferably a vasodilator, is administered to the urethra of the individual undergoing treatment for PVD or a related vascular disease such as Leriche's syndrome. Preferred vasoactive agents include, but are not limited to: naturally occurring prostaglandins such as $PGE_0$, $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$; and semisynthetic or synthetic derivatives of natural prostaglandins, including those having the structure of Formula (I) as defined hereinabove, and including, specifically, carboprost tromethamine, dinoprost tromethamine, dinoprostone, lipoprost, gemeprost, metenoprost, sulprostone and tiaprost. Prostaglandins $E_0$, $E_1$ and $E_2$ are particularly preferred vasodilators for use in conjunction with the present method. Simultaneous administration of two or more vasodilating agents may in some cases be desirable and exhibit a synergistic effect.

Suitable vasoactive agents also include vasoactive intestinal polypeptide and derivatives thereof, particularly derivatives in the form of hydrolyzable lower alkyl esters. "Vasoactive intestinal polypeptide" is also referred to as neuroactive polypeptide gastrointestinal hormone, and, as known in the art, exhibits a wide variety of biological activities, including relaxation of systemic and vascular smooth muscle.

The active agents may be administered in the form of pharmaceutically acceptable salts or esters, or combinations thereof. Salts and esters of the active agents may be prepared using standard procedures known to those skilled in the art of synthetic organic chemistry and described, for example, by J. March, *Advanced Organic Chemistry: Reactions, Mechanisms and Structure*, 4th Ed. (New York: Wiley-Interscience, 1992). For example, acid addition salts are prepared from the free base (typically wherein the neutral form of the drug has a neutral —$NH_2$ group) using conventional means, involving reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of acid moieties which may be present on a drug are prepared in a similar manner using a pharmaceutically acceptable base such as sodium hydroxide, potassium hydroxide, ammonium hydroxide, calcium hydroxide, trimethylamine, or the like. Preparation of esters involves functionalization of hydroxyl and/or carboxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures.

Pharmaceutical Formulations and Modes of Administration

The active agent is, as explained above, administered in a pharmaceutical formulation suitable for transurethral drug delivery. The formulation contains one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred.

Depending on the drug administered, it may be desirable to incorporate a transurethral permeation enhancer in the urethral dosage form. Examples of suitable transurethral permeation enhancers include dimethylsulfoxide ("DMSO"), dimethyl formamide ("DMF"), N,N-dimethylacetamide ("DMA"), decylmethylsulfoxide ("$C_{10}MSO$"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), SEPA® (available from Macrochem Co., Lexington, Md.), lower alkanols, (e.g., ethanol), surfactants as discussed above, including, for example, Tergitol®, Nonoxynol-9® and TWEEN-80®).

Transurethral formulations may additionally include one or more enzyme inhibitors effective to inhibit drug-degrading enzymes which may be present in the urethra. Such enzyme inhibiting compounds may be determined by those skilled in the art by reference to the pertinent literature and/or using routine experimental methods. Generally, then, these compounds will be such that they inhibit enzymes (or their cofactors, e.g., NAD, NADP, ATP) present in situ which could degrade or metabolize the active agent. For example, with a prostaglandin as the active agent, a compound effective to inhibit prostaglandin-degrading enzymes may be included, e.g., an inhibitor of 15-hydroxy-prostaglandin dehydrogenase, 13-prostaglandin reductase or prostaglandin 9-keto-reductase, all of which are present in the urethra, the ureters and the local lower genitourinary tract. Such compounds will include, for example, fatty acids, fatty acid esters, and NAD inhibitors. Preferred fatty acids are those containing 12–20 carbon atoms and 0–4 double bonds, including, but not limited to, lauric acid, stearic acid, linolenic acid, arachidonic acid, and the like. Preferred fatty acid esters are those formed from lower alkanols and 1–3 fatty acid chains, with the fatty acids selected from those just described.

Additional optional components include excipients, preservatives (e.g., antioxidants), chelating agents, solubilizing agents (e.g., surfactants), and the like, as will be appreciated by those skilled in the art of drug formulation preparation and delivery.

Transurethral drug administration, as explained in co-pending patent application Ser. No. 07/514,397, entitled "Treatment of Erectile Dysfunction" (published internationally as WO91/16021), can be carried out in a number of different ways using a variety of urethral dosage forms. For example, the drug can be introduced into the urethra from a flexible tube, squeeze bottle, pump or aerosol spray. The drug may also be contained in coatings, pellets or suppositories which are absorbed, melted or bioeroded in the urethra. In certain embodiments, the drug is included in a coating on the exterior surface of a penile insert. A preferred drug delivery device for administering a drug transurethrally is shown in FIG. 1. It is preferred, although not essential, that the drug be delivered at least about 3 cm into the urethra, and preferably at least about 7 cm into the urethra. Generally, delivery at about 3 cm to about 8 cm into the urethra will provide effective results in conjunction with the present method.

Urethral suppository formulations containing PEG or a PEG derivative are particularly preferred urethral dosage forms herein, and may be conveniently formulated using conventional techniques, e.g., compression molding, heat molding or the like, as will be appreciated by those skilled in the art and as described in the pertinent literature and pharmaceutical texts. See, for example, *Remington: The Science and Practice of Pharmacy*, 19th Ed. (Easton, Pa.: Mack Publishing Co., 1995), which discloses typical methods of preparing pharmaceutical compositions in the form of urethral suppositories. The PEG or PEG derivative preferably has a molecular weight $M_w$ in the range of about 200 to 2500, more preferably in the range of about 1000 to 2000. Suitable polyethylene glycol derivatives include polyethylene glycol fatty acid esters, for example, polyethylene glycol monostearate, polyethylene glycol sorbitan esters, e.g., polysorbates, and the like. It is also preferred that urethral suppositories contain one or more solubilizing agents effective to increase the solubility of the active agent in the PEG or other transurethral vehicle.

The solubilizing agent may be a nonionic, anionic, cationic or amphoteric surfactant. Nonionic surfactants include: long-chain fatty acids, i.e., acids having the structural formula $CH_3(CH_2)_m COOH$ where m is an integer in the range of 8 to 16; fatty alcohols, that is, alcohols having the structural formula $CH_3(CH_2)_m C(H)OH$, such as lauryl, cetyl and stearyl alcohols; glyceryl esters such as the naturally occurring mono-, di- and triglycerides; and esters of fatty alcohols or other alcohols such as propylene glycol, polyethylene glycol, sorbitan, sucrose, and cholesterol. Examples of water-soluble nonionic surfactant derivatives include sorbitan fatty acid esters (such as those sold under the tradename Span®), polyoxyethylene sorbitan fatty acid esters (such as those sold under the tradename Tween®), polyoxyethylene fatty acid esters (such as those sold under the tradename Myrj®), polyoxyethylene steroidal esters, polyoxypropylene sorbitan fatty acid esters, polyoxypropylene fatty acid esters, polyoxypropylene steroidal esters, polyoxyethylene ethers (such as those sold under the tradename Brij®), polyglycol ethers (such as those sold under the tradename Tergitol®), and the like. Preferred nonionic surfactants for use as the solubilizing agent herein are polyglycol ether, polyoxyethylene sorbitan trioleate, sorbitan monopalmitate, polysorbate 80, polyoxy-ethylene 4-lauryl ether, propylene glycol, and mixtures thereof. Anionic surfactants which may be used as the solubilizing agent herein include long-chain alkyl sulfonates, carboxylates, and sulfates, as well as alkyl aryl sulfonates, and the like. Preferred anionic surfactants are sodium dodecyl sulfate, dialkyl sodium sulfosuccinate (e.g., sodium bis-(2-ethylhexyl)-sulfosuccinate), sodium 7-ethyl, 2-methyl, 4-docyl sulfate and sodium dodecylbenzene sulfonate. Cationic surfactants which may be used to solubilize the active agent are generally long-chain amine salts or quaternary ammonium salts, e.g., decyltrimethylammonium bromide, dodecyltrimethyl-ammonium bromide, tetradecyltrimethylammonium bromide, tetradecyltrimethylammonium chloride, and the like. Amphoteric surfactants are generally, although not necessarily, compounds which include a carboxylate or phosphate group as the anion and an amino or quaternary ammonium moiety as the cation. These include, for example, various polypeptides, proteins, alkyl betaines, and natural phospholipids such as lecithins and cephalins. Other suitable solubilizing agents (e.g., glycerin) may also be used, as will be appreciated by those skilled in the art. The solubilizing agent will be present in the range of approximately 0.01 wt. % to 40 wt. %, more preferably in the range of approximately 5.0 wt. % to 40 wt. %, and most preferably in the range of approximately 10.0 wt. % to 40 wt. %.

It may be desirable to deliver the active agent in a urethral dosage form which provides for controlled or sustained release of the active agent. In such a case, the dosage form typically comprises a biocompatible, biodegradable material, typically a biodegradable polymer. Examples of such polymers include polyester, polyalkyl-cyanoacrylate, polyorthoester, polyanhydride, albumin, gelatin and starch. As explained, for example, in International Patent Publication No. WO96/40054, these and other polymers can be used to provide biodegradable microparticles which enable controlled and sustained drug release, in turn minimizing the required dosing frequency.

The urethral suppository will preferably, although not necessarily, be on the order of 2 to 20 mm, preferably 5 to 10 mm in length and less than about 5 mm, preferably less than about 2 mm in width. The weight of the suppository form will typically be in the range of approximately 1 mg to 100 mg, preferably in the range of approximately 1 mg to 50 mg. However, it will be appreciated by those skilled in the art that the size of the suppository can and will vary, depending on the potency of the drug, the nature of the formulation, and other factors.

In FIG. 1, a suitable transurethral drug delivery device is shown generally at 10. The device comprises a transurethral inserter 11 having an easily graspable segment 12 that has opposing symmetrically concave surfaces 13 and 14 adapted to be held by two fingers. Drug is contained within a urethral suppository (not shown) within shaft 15, which is sized to fit within the urethra. A longitudinal plunger, the tip of which is seen at 16, is slidably insertable into the longitudinal bore contained within shaft 15. To extrude drug into the urethra, shaft 15 is inserted into the urethra, and plunger tip 16 is pushed into segment 12. The inserter 11 is then removed. Prior to use, and during storage, the device is capped with elongate cap 17 which fits snugly over flange 18 at the proximal end of shaft 15. The cap 17 is provided with a series of parallel ridges 19 to facilitate gripping of the cap and removal from inserter 11.

Although the transurethral drug delivery device shown in FIG. 1 represents a preferred device for use herein, again, it should be emphasized that a wide variety of device configurations and urethral dosage forms can be used.

Examples of other devices suited to deliver a drug transurethrally are those described and illustrated in WO 91/16021.

The devices can either be manufactured under sterile conditions, thereby eliminating the need for post-manufacturing sterilization, or they can be manufactured under non-sterile conditions and then subsequently sterilized by any suitable technique, e.g., radiation sterilization. The devices can be manufactured by typical plastic forming and coating processes known in the art, including molding extrusion, heat forming, dip coating, and the like.

The method of drug delivery herein may involve an "active" delivery mechanism such as iontophoresis, electroporation or phonophoresis. Devices and methods for delivering drugs in this way are well known in the art. Iontophoretically assisted drug delivery is, for example, described in PCT Publication No. WO96/40054, cited above. Briefly, the active agent is driven through the urethral wall by means of an electric current passed from an external electrode to a second electrode contained within or affixed to a urethral probe.

In addition to the uses discussed hereinabove, the transurethral administration of vasoactive agents as now provided is useful in the treatment of a variety of cardiovascular and pulmonary conditions and disorders. By "cardiovascular" conditions and disorders is meant a general category that includes congenital heart disease, rheumatic heart disease, coronary heart disease and cerebrovascular disease. Examples of cardiovascular and pulmonary conditions and disorders which may be treated using the methods and formulations of the invention include, but are not limited to: angina pectoris and the like; cardiac arrhythmias; atrioventricular node dysfunctions; acute respiratory distress syndrome; emphysema; asthma; and pulmonary hypertension.

Kits

The invention also encompasses a kit for patients to carry out the aforementioned method. The kit contains the pharmaceutical formulation to be administered, a device for administering the formulation (e.g., a transurethral drug delivery device such as shown in FIG. 1), a container, preferably sealed, for housing the drug and device during storage and prior to use, and instructions for carrying out drug administration in an effective manner. The formulation may consist of the drug in unit dosage form. The kit may contain multiple formulations of different dosages of the same agent. The kit may also contain multiple formulations of different active agents. The instructions may be in written or pictograph form, or can be on recorded media including audio tape, video tape, or the like.

Use in Conjunction with Venous Flow Control ("VFC") Device

In an alternative embodiment of the invention, the pharmacologically active agent is administered in combination with a venous flow control device such as that described in commonly assigned U.S. patent application Ser. No. 08/782, 867, filed Jan. 10, 1997, entitled "Venous Flow Control Element for Maintaining Penile Erection." Preferred devices are formed from a length of flexible tubing having an integral fastening means, so as to provide for readily adjustable venous flow control when applied to the penis. The device is applied to the base of the penis prior to and during sexual intercourse, such that it effectively enhances retention of blood within the penis without substantially obstructing arterial inflow or becoming too constrictive during the erectile process. Use of the VFC device also enables enhanced effectiveness of local drug therapy, in that the active agent is retained within the penis, allowing movement into the corpus cavernosa. This produces smooth muscle response and a consistent erectile response. In this embodiment, a kit will include the venous flow control device in addition to the components noted above, along with instructions for using the device.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

A pharmaceutical formulation containing a vasodilating agent for transurethral administration is prepared by mixing polyethylene glycol, molecular weight ($M_w$) approximately 4000, with an amount of prostaglandin $PGE_1$ sufficient to provide a total of 0.5 mg in the formulation, and heating the mixture to a temperature just high enough to produce an $E_1$-polymer melt. The prostaglandin-glycol mixture can then be poured into a mold suitable to provide a $PGE_1$ suppository approximately 5 mm in diameter and 12.5 mm in length, and allowed to cool. The suppository so provided is a unit dosage form suitable for transurethral administration. If desired, the $PGE_1$-glycol mixture may be allowed to cool on the tip of a rod adapted to be inserted into the urethra.

EXAMPLE 2

The procedure of Example 1 is repeated, except that a final amount of 0.2 mg prostaglandin $E_2$ is substituted for $PGE_1$. A suppository suitable for transurethral administration of a unit dosage of the vasoactive agent is thus provided.

EXAMPLE 3

The procedure of Examples 1 and 2 are repeated, except that cocoa butter is substituted for polyethylene glycol.

EXAMPLE 4

A pharmaceutical formulation containing a vasodilating agent for urethral administration is prepared by dispersing prostaglandin $E_1$ in a sufficient quantity of glycerin to equal 70% of the final suppository weight. Pharmagel A or B (30%) is then added. Suppositories are then prepared as described in Example 1.

EXAMPLE 5

The procedure of Example 4 is repeated, except that prostaglandin $E_2$ is substituted for $PGE_1$. A suppository suitable for transurethral administration of a unit dosage of the vasoactive agent is thus provided.

EXAMPLE 6

A penile insert coated with $PGE_1$ is prepared as follows. An ethylene vinyl acetate (28% VA) rod is formed into an insert having a shaft with a spherical, blunted tip and a head portion. A dipping bath comprising a 50—50 weight blend of PEG 1450 and PEG 4000 and sufficient $PGE_1$ to provide for 0.5 mg in total coating is prepared and heated to 70° C. The insert is suspended by its head, dipped into the dipping bath and removed. A penile insert suitable for transurethral administration of $PGE_1$ is thus provided.

EXAMPLE 7

The procedure of Example 6 is repeated, except that 0.2 mg prostaglandin $PGE_2$ is substituted for 0.5 mg of $PGE_1$.

EXAMPLE 8

A $PGE_1$ gel is prepared as follows. $PGE_1$ is mixed with 2% xylocaine jelly and a pharmaceutically acceptable lubricant such as K-Y surgical lubrication jelly (hydroxyethylcellulose, available from Johnson & Johnson). Mixing is conducted by stirring until a homogeneous mixture is obtained. A $PGE_1$ gel formulation having approximately 1.6 mg of $PGE_1$ per 2 cc gel is optimal.

EXAMPLE 9

The procedure of Example 8 is repeated, except that prostaglandin $PGE_2$ is substituted for $PGE_1$.

EXAMPLE 10

Individuals are assessed and pre-screened to assemble an experimental group of subjects suffering from intermittent claudication. Each individual is affected by peripheral arterial insufficiency at the second stage of Fontaine's classification (i.e., claudication on effort without pain at rest and/or trophic in an affected leg) for at least a year prior to enrollment in the study. Ankle/brachial systolic blood pressure ratio is obtained by Doppler ultrasound. Blood perfusion is measured by impedance plethysmography using the method of Nyober et al. (1974) *A. Heart J.* 87:704, and calculated from an average of five consecutive waves. Walking distance before the occurrence of claudication is measured on a treadmill and expressed as absolute walking distance (AWD) which indicates the maximum distance in meters walked by the individual at an average speed 2.5 mph on a grade of 7 degrees.

The effect of transurethral treatment using the pharmaceutical formulations of the invention is assessed as follows. Individuals are treated using transurethral administration of an effective amount of one of the pharmaceutical formulations of Examples 1–9. The treatments are administered twice daily. At the end of a three week treatment period, blood flow and ankle/brachial systolic blood pressure ratios are measured in the affected limb at rest. Individuals then perform the above-described treadmill test to assess AWD. Subjective symptoms, such as coldness, paresthesias, limb fatigue and pain during the treadmill test are also monitored. Intensity of each subjective symptom is scored on a six-point scale: 6=(total relief), 5=(marked improvement), 4=(slight improvement), 3=(no change), 2=(slight deterioration), 1=(marked deterioration).

It is expected that the treatments of the invention will give rise to an average 20% increase in AWD, and will substantially alleviate the subjective symptoms.

We claim:

1. A method for treating peripheral vascular disease (PVD) or a related vascular disease in an individual in need of such treatment, comprising transurethrally administering to the individual an effective amount of a pharmaceutical formulation containing a vasoactive agent by placing the pharmaceutical formulation in contact with the male urethra at a location between the proximal portion of the fossa navicularis and the distal portion of the pendulous urethra, such that the vasodilating agent enters the individual's blood stream through the urethral wall.

2. The method of claim 1, wherein the vasoactive agent is a vasodilating agent.

3. The method of claim 2, wherein the vasodilating agent is selected from the group consisting of naturally occurring prostaglandins, synthetic prostaglandin derivatives, and mixtures thereof.

4. The method of claim 3, wherein the vasodilating agent is a naturally occurring prostaglandin.

5. The method of claim 4, wherein the naturally occurring prostaglandin is selected from the group consisting of $PGE_0$, $PGE_1$, $PGA_1$, $PGB_1$, $PGF_{1a}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$ and $PGF_{3a}$.

6. The method of claim 5, wherein the naturally occurring prostaglandin is $PGE_0$.

7. The method of claim 5, wherein the naturally occurring prostaglandin is $PGE_1$.

8. The method of claim 5, wherein the naturally occurring prostaglandin is $PGE_2$.

9. The method of claim 3, wherein the vasodilating agent is a synthetic prostaglandin derivative.

10. The method of claim 9, wherein the synthetic prostaglandin derivative is selected from the group consisting of carboprost tromethamine, dinoprost tromethamine, dinoprostone, gemeprost, metenoprost, sulprostone and tiaprost.

11. The method of claim 1, wherein the pharmaceutical formulation further comprises an effective enhancing amount of a transurethral permeation enhancer.

12. The method of claim 3, wherein the pharmaceutical formulation further comprises an enzyme-inhibiting amount of a compound effective to inhibit prostaglandin-degrading enzymes.

13. The method of claim 12, wherein the inhibitor is selected from the group consisting of fatty acids having from 12–20 carbon atoms and 0–4 double bonds, fatty acid esters formed from lower alkanols and 1–3 fatty acid chains having from 12–20 carbon atoms and 0–4 double bonds, and NAD inhibitors.

14. The method of claim 1, wherein the pharmaceutical formulation contains an additional pharmacologically active agent.

15. The method of claim 14, wherein the additional pharmacologically active agent is a second vasoactive agent.

16. The method of claim 15, wherein the second vasoactive agent is a vasodilating agent.

17. A method for treating vascular impotence associated with peripheral vascular disease (PVD) or a related vascular disease in an individual, comprising transurethrally administering to an individual in need of such treatment a transurethral pharmaceutical formulation containing an effective amount of a vasoactive agent by placing the pharmaceutical formulation in contact with the male urethra at a location between the proximal portion of the fossa navicularis and the distal portion of the pendulous urethra, such that the vasodilating agent enters the individual's blood stream through the urethral wall.

18. The method of claim 17, wherein the vasoactive agent is a vasodilating agent.

19. The method of claim 18, wherein the vasodilating agent is selected from the group consisting of naturally occurring prostaglandins, synthetic prostaglandin derivatives, and mixtures thereof.

20. The method of claim 19, wherein the vasodilating agent is a naturally occurring prostaglandin.

21. The method of claim 20, wherein the naturally occurring prostaglandin is selected from the group consisting of $PGE_0$, $PGE_1$, $PGA_1$, $PGB_1$, $PGF_{1a}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$ and $PGF_3$.

22. The method of claim 21, wherein the naturally occurring prostaglandin is $PGE_0$.

23. The method of claim 21, wherein the naturally occurring aäostaglandin is $PGE_1$.

24. The method of claim 21, wherein the naturally occurring prostaglandin is $PGE_2$.

25. The method of claim 19, wherein the vasodilating agent is a synthetic prostaglandin derivative.

26. The method of claim 25, wherein the synthetic prostaglandin derivative is selected from the group consisting of carboprost tromethamine, dinoprost tromethamine, dinoprostone, gemeprost, metenoprost, sulprostone and tiaprost.

27. The method of claim 17, wherein the pharmaceutical formulation further comprises an effective enhancing amount of a transurethral permeation enhancer.

28. The method of claim 19, wherein the pharmaceutical formulation further comprises an enzyme-inhibiting amount of a compound effective to inhibit prostaglandin-degrading enzymes.

29. The method of claim 28, wherein the inhibitor is selected from the group consisting of fatty acids having from 12–20 carbon atoms and 0–4 double bonds, fatty acid esters formed from lower alkanols and 1–3 fatty acid chains having from 12–20 carbon atoms and 0–4 double bonds, and NAD inhibitors.

30. The method of claim 18, wherein the pharmaceutical formulation contains an additional pharmacologically active agent.

31. The method of claim 30, wherein the additional pharmacologically active agent is a second vasoactive agent.

32. The method of claim 31, wherein the second vasoactive agent is a vasodilating agent.

33. A kit for treating peripheral vascular disease (PVD) in an individual in need of such treatment, comprising:
(a) an effective amount of a pharmaceutical formulation containing a vasodilating agent selected from the group consisting of naturally occurring prostaglandins, synthetic prostaglandin derivatives, and mixtures thereof;
(b) a drug delivery means for administering the pharmaceutical formulation transurethrally;
(c) container means for housing the pharmaceutical formulation and drug delivery means; and
(d) instructions for using the pharmaceutical formulation and drug delivery means to administer the vasodilating agent transurethrally within the context of a regimen effective to treat PVD or a related vascular disease.

34. A kit for treating vascular impotence associated with peripheral vascular disease (PVD) or a related vascular disease in an individual in need of such treatment, comprising:
(a) an effective amount of a pharmaceutical formulation containing a vasodilating agent selected from the group consisting of naturally occurring prostaglandins, synthetic prostaglandin derivatives, and mixtures thereof;
(b) a drug delivery means for administering the pharmaceutical formulation transurethrally;
(c) container means for housing the pharmaceutical formulation and drug delivery means; and
(d) written instructions for using the pharmaceutical formulation and drug delivery means to administer the vasodilating agent transurethrally within the context of a regimen effective to treat vascular impotence associated with PVD or a related vascular disease.

35. A pharmaceutical formulation for treating peripheral vascular disease in an individual in need of such treatment, comprising a urethral suppository containing a therapeutically effective amount of a vasodilating agent selected from the group consisting of naturally occurring prostaglandins, synthetic prostaglandin derivatives, and mixtures thereof, a vehicle suitable for transurethral drug delivery, and, optionally, an enzyme-inhibiting amount of a compound effective to inhibit prostaglandin-degrading enzymes, and a suppository base suitable for transurethral drug delivery comprising polyethylene glycol having a molecular weight in the range of approximately 200 to 2500 wherein the therapeutically effective amount of the vasodilating agent is such that the composition is effective to treat peripheral vascular disease when administered transurethrally, and further wherein the suppository is approximately 2 to 20 mm in length and less than approximately 2 mm in width.

36. The pharmaceutical formulation of claim 35, containing a compound effective to inhibit prostaglandin-degrading enzymes.

37. The pharmaceutical formulation of claim 36, wherein the compound effective to inhibit prostaglandin-degrading enzymes is selected from the group consisting of fatty acids having from 12–20 carbon atoms and 0–4 double bonds, fatty acid esters formed from lower alkanols and 1–3 fatty acid chains having from 12–20 carbon atoms and 0–4 double bonds, and NAD inhibitors.

38. The pharmaceutical formulation of claim 35, further including an effective amount of a transurethral permeation enhancer.

39. The pharmaceutical formulation of claim 35, further including an additional pharmacologically active agent.

40. The pharmaceutical formulation of claim 39, wherein the additional pharmacologically active agent is a second vasodilating agent.

41. The pharmaceutical formulation of claim 35, further including one or more components selected from the group consisting of surfactants, stabilizers and preservatives.

42. A pharmaceutical formulation for treating vascular impotence, comprising:
(a) a vasodilating agent selected from the group consisting of $PGE_0$, $PGE_1$ and $PGE_2$;

(b) an enzyme-inhibiting amount of a compound effective to inhibit prostaglandin-degrading enzymes, selected from the group consisting of fatty acids having from 12–20 carbon atoms and 0–4 double bonds, fatty acid esters formed from lower alkanols and 1–3 fatty acid chains having from 12–20 carbon atoms and 0–4 double bonds, and NAD inhibitors;

(c) an effective enhancing amount of a transurethral permeation enhancer;

(d) a carrier suitable for transurethral drug delivery; and (e) one or more components selected from the group consisting of surfactants, stabilizers and preservatives.

* * * * *